United States Patent [19]

Wiksell

[11] Patent Number: 4,974,581
[45] Date of Patent: Dec. 4, 1990

[54] ULTRASONIC KNIFE

[75] Inventor: Hans Wiksell, Taby, Sweden

[73] Assignee: Swedemed AB, Uppsala, Sweden

[21] Appl. No.: 428,009

[22] Filed: Oct. 30, 1989

Related U.S. Application Data

[63] Continuation of Ser. No. 125,632, Nov. 25, 1987, abandoned.

[30] Foreign Application Priority Data

Sep. 4, 1987 [SE] Sweden .............................. 8703458-3

[51] Int. Cl.$^5$ .............................................. A61H 23/00
[52] U.S. Cl. ..................................... 128/24 A; 604/22
[56] References Cited

U.S. PATENT DOCUMENTS

| | | | |
|---|---|---|---|
| 4,169,984 | 10/1979 | Parisi | 128/24 A X |
| 4,330,278 | 5/1982 | Martin | 128/24 A X |
| 4,526,571 | 7/1985 | Wuchinich | 128/24 A X |
| 4,535,759 | 8/1985 | Polk et al. | 128/24 A |
| 4,561,438 | 12/1985 | Bonnet et al. | 128/24 A X |
| 4,634,419 | 1/1987 | Kreizman et al. | 128/24 A X |

Primary Examiner—Francis Jaworski
Attorney, Agent, or Firm—Armstrong, Nikaido, Marmelstein, Kubovcik & Murray

[57] ABSTRACT

A curved ultrasonic knife consisting of a transducer unit (5) and an amplitude-amplifying horn connected directly thereto, the knife being shaped to imbue the tip (43) of the horn with, to a great extent, purely longitudinal oscillation. The transducer unit includes a piezoelectric unit axially clamped in the transducer unit (5). A resonance rod (28) located between the piezoelectric unit and the horn (2) is bent to give a deflection of 16°, for example.

8 Claims, 1 Drawing Sheet

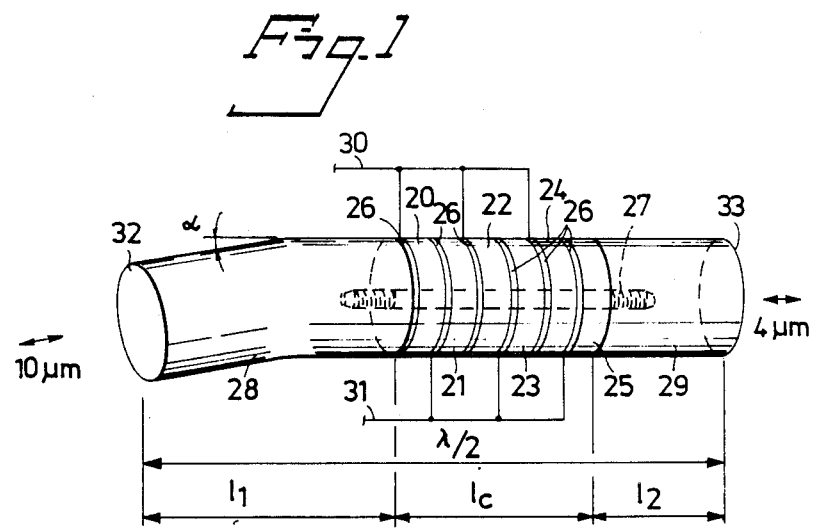
Fig. 1
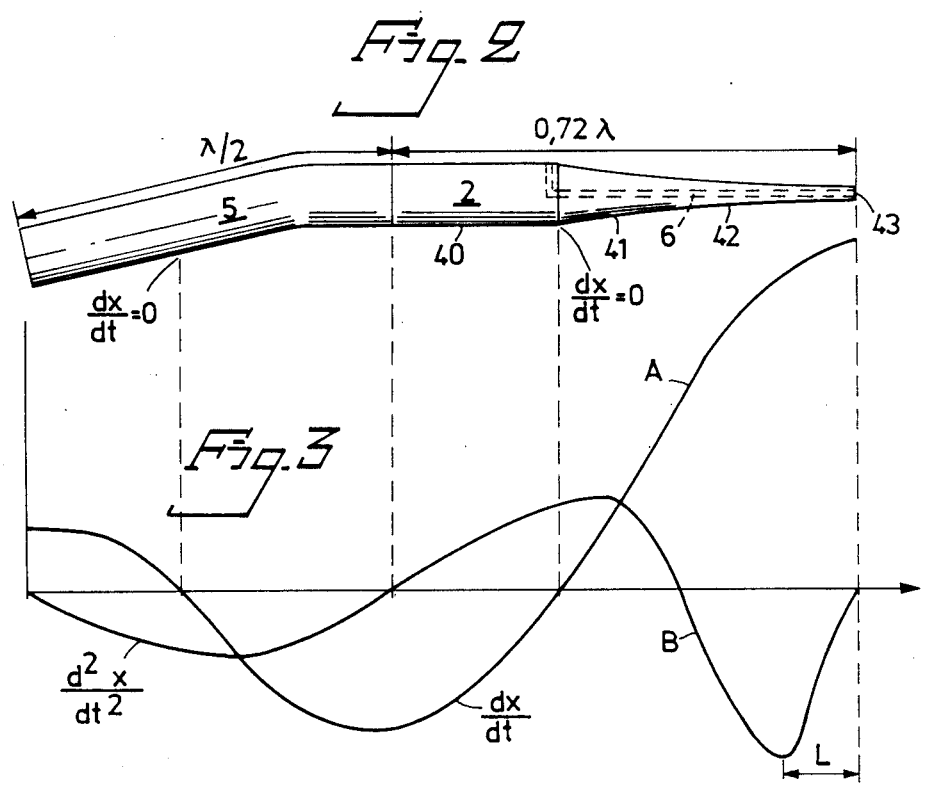
Fig. 2
Fig. 3

ULTRASONIC KNIFE

This application is a continuation of application Ser. No. 125,632 filed Nov. 25, 1987 and now abandoned.

The present invention relates to an ultrasonic knife consisting of a horn with a tip to be brought into contact with tissue, and a transducer unit connected to the opposite end of the horn and arranged to imbue the tip with a longitudinal oscillation.

Particularly in connection with surgery on the brain stem or spinal region, i.e. when a stereomicroscope is used for maximum efficiency the ultrasonic knife should be designed with a curved arrangement so that its rear end containing the transducer system, inter alia, does not disturb the line of vision between microscope and operating point.

An ultrasonic knife of the type in question is already known through Swedish patent application 85 05 289-2. The transducer unit here is straight and has a length of 0.5 lambda, lambda referring to the wavelength of the relevant longitudinal vibration. The horn has a length of approximately 0.7 lambda in order to give a suitable amplitude amplification.

Extensive research and development work was required to achieve an ultrasonic knife which would work in the desired manner with high efficiency and extremely clean-cut longitudinal oscillation in a non-linear oscillation mode for the tip. The result of this research is described in said Swedish published specification where it is stated, inter alia, that the transducer unit shall have a length of 0.5 lambda, this length thus depending on the vibration frequency, distribution speed in the longitudinal direction in the transducer material, and the ratio between length and cross section in the transducer unit.

As is also stated in the Swedish patent application, it may be suitable for the transducer unit to have a resonance rod which is not symmetrical in longitudinal direction. The vibration amplitude will therefore be greater at the end of the transducer unit which is connected to the horn.

Furthermore, when designing the transducer unit it must also be taken into consideration that the ratio between length and cross-sectional area may be critical for the occurrence of disturbing sound phenomena even at low frequencies.

The longitudinal vibration of the transducer must then be amplified by a suitably shaped "horn", preferably shaped as described in the Swedish application and having a length of about 0.72 lambda.

From the above it is clear that the transducer and the horn cooperate to generate a well-defined movement in the working tip of the horn, and it will be realized that a large number of parameters of geometric nature and relating to material and electro-engineering cooperate in complete accord both acoustically and with respect to resonance for this purpose.

A known ultrasonic knife thus includes a straight transducer with a length of 0.5 lambda and a straight horn about 0.7 lambda connected thereto. The total length of a knife made of Duralumin or a suitable titanium alloy with a frequency of 24 kHz and a transducer diameter about 16 mm, will be about 250 mm.

As is well known to one skilled in the art, and is also stated in said patent application, the transducer and horn can be joined together via a waveguide which should have a length which is an integer multiple of 0.5 lambda. Such a waveguide preferably consists of a hard material giving low losses, such as titanium, Duralumin or magnesium. With the inclusion of such a waveguide the total length of the ultrasonic knife will be about 350 mm for a frequency of 24 kHz and using materials of the type mentioned.

Such an increase in length is normally only justified in that it allows a slight curve in said waveguide. A curved ultrasonic knife is thus available for applications of the nature mentioned in the introduction.

However, it will also be realized that the known feasibility of making the knife curved also means that its length and weight must be considerably increased, which has a negative effect on its manoeuvrability.

It has now proved possible to achieve a curved ultrasonic knife of the type described with no waveguide between the transducer unit and the horn, without causing any significant difference in performance from a straight knife design of the type discussed.

According to the invention, this advantage is achieved by the transducer unit being provided with a curved resonance rod.

Thus it has surprisingly been found that a curved design of the resonance rod in the transducer unit does not unfavourably affect the delicate parameter balance prevailing in the known ultrasonic knives discussed. However, the length of this curved resonance rod in the transducer must be adjusted. In comparison with the straight resonance rod, the length of the curved resonance rod must be adjusted to give resonance at the intended frequency, usually 24 kHz nominal frequency. This is because the longitudinal waves must travel different phase distances depending on the difference in route caused by respective radii of curvature. According to the invention a length is preferably selected which restores the mean value for said varying curve radius. The deflection of the resonance rod is about 16°, for instance.

A suitable transducer unit is of the general design described in the cited application and comprises a short and a longer rod part between which a stack of piezo-electric elements are clamped so that the resultant transducer unit has higher amplitude at one end than at the other, the horn which amplifies the amplitude being suitably connected to said one end of the unit.

An example of a curved ultrasonic knife according to the invention with no curved waveguide between the transducer unit and the horn will now be described with reference to the accompanying drawings.

FIG. 1 shows schematically a transducer unit included in the ultrasonic knife according to the invention, FIG. 2 shows schematically a side view of the central components in the ultrasonic knife according to the invention; and FIG. 3 is a diagram illustrating the amplitude distribution in longitudinal direction for the ultrasonic knife according to FIG. 2 and also shows the magnitude of material stress along the length of the ultrasonic knife.

As can be seen in FIG. 2, the ultrasonic knife is composed substantially of a transducer unit 5 and a knife portion 2 in the form of a "horn". A person skilled in the art will appreciate that a horn may be connected to the transducer unit 5 at that point where the longitudinal vibration is maximal, for instance. He will also appreciate that any connections to the horn 2, together with seals such as an 0-ring, are suitably located at the point along the horn where the longitudinal vibration amplitude is least.

The knife of course also has a connection for the supply of alternating voltage of ultrasonic frequency to the part of the transducer unit 5 which generates vibration, via leads 30 and 31. The horn 2 is an amplitude transformer, its geometry being described below.

A bore 6 extends centrally through the tip of the horn and may be connected to an aspiration tube. A tube for the supply of saline solution to the tip of the knife may also be attached.

The transducer unit in FIGS. 1 comprises a piezoelectric element or oscillating portion having six rings 20–25 of a sintered ceramic material, between which are inserted holed discs 26 of copper-beryllium alloy, for instance. The rings 20–25 and discs 26 are arranged on a titanium pin 27 threaded at both ends. The pin is also provided with a layer (not shown) of electrically insulating material, teflon, to serve as electrical insulation for the discs 26. Cylindrical resonance rods 28, 29 made of a magnesium alloy or the like are screwed into each end of the pin 27 and the whole unit 20–29 is statically prestressed to give a pressure of about 500 kg/cm² enabling it to withstand the considerable acceleration to which they are subjected when the voltage is transmitted over the leads 30, 31. These leads are electrically connected to the discs 26 in such a way that one is connected to alternate discs while the other is connected to the remaining discs.

The length of the transducer unit is half a wavelength for the alternating supply voltage. The resonance rods 28, 29 are of different lengths, $L_1$ and $L_2$, calculated as follows if the rods are straight $$\frac{\omega_c l}{v_c} + \tan^{-1}\left[\left[\frac{A_1 - P_1 - v_1}{A_c - P_c - v_c}\right] - \tan\left[\frac{\omega_1 l}{v_1}\right]\right] +$$
$$+ \tan^{-1}\left[\left[\frac{A_2 - P_2 - v_2}{A_c - P_c - v_c}\right] - \tan\left[\frac{\omega_2 l}{v_2}\right]\right] = \pi$$

where $f = \frac{\omega}{2\pi}$ and where $l_1, l_2, l_c$ denote the length of the rods 28, 29 or the length of the ring unit 20–25, $v_1, v_2, v_c$ denote the velocity of sound for the same units, $A_1, A_2, A_c$ denote the cross-sectional area of these units, and $P_1, P_2, P_c$ denote the density of these units.

However, since according to the invention one of the resonance rods, preferably resonance rod 28, is curved, the deflection being 16°, for instance, the length $L_1$ is modified since the longitudinal waves must travel different phase distances depending on the different route caused by respective radii of curvature for the curved portion. A length is preferably selected which restores the mean value for said varying curve radius.

According to a preferred embodiment of the knife device shown in the drawing, a suitable ratio $l_1:l_2$ is 2.5 so that the transducer oscillates with a stroke of about 10 μm at the end surface 32 and 4 μm at the end surface 33. The amplitude transformer 2, preferably about 0.72 λ in length, is connected to the end surface 32 of the transducer and amplifies the magnitude of the movement about 30 times.

The transducer unit and the amplitude transformer are held together by means of a bolt, connected by a screw joint, for instance, to the two rods 28, 29.

The amplitude transformer utilized is preferably made of a titanium alloy including aluminium and vanadium. The iron content should not exceed 0.3%. The amplitude transformer includes three sections 40, 41, 42. Section 40 is cylindrical in shape and merges into section 41, the geometry of which is a wave function of the fourth order Fourier form, i.e.

$$U(X) = \sum_{n=0}^{n=3} a_K \cdot \cos K \cdot \pi \cdot X$$

where

U(X) = longitudinal deflection in X-direction $a_K$ = constants

Section 42 is substantially tapering. With this embodiment of the knife a pronounced resonance is obtained related to the longitudinal oscillation movement, and from the frequency aspect, this resonance is widely separated from the secondary longitudinal resonances and remaining resonances related to transverse oscillations. From the diagram in FIG. 3, taken in conjunction with FIG. 1, where the abscissa relates to the length of the amplitude transformer according to curves A and B, and the ordinate relates to the longitudinal oscillation according to curve A and the magnitude of material stress according to curve B, it will be seen that knife stroke reaches its maximum at point 43 and decreases towards 0 at the point where the bore 6 opens out on the surface. It is thus possible to seal the connection of the vacuum tube to the bore with 0-ring seals which will not be affected by vibration. For the same reason, the handle is attached to the transducer 5 to prevent it vibrating in the operator's hand. Curve B also shows that material stresses are at a maximum not at the outermost tip 43, but in a region situated a distance L inside this tip. The advantage of this geometry of the knife is obvious in that it gives increased service life. The resonance points of the knife can easily be checked experimentally by connecting it to the transducer and supplying the latter with electrical energy of ultrasonic frequency. The movement of the tip 43 can thus be measured.

Through the invention, therefore, despite the curved form of the knife, it is possible to achieve unlimited amplitude, i.e. "full" data can be achieved in the form of an amplitude of 300 (240) micrometer for the tip 43. Despite this, the device functions efficiently and the loss factor is thus satisfactory, which in turn ensures that the power development in the transducer unit 5 is acceptable. It is thus possible according to the invention to produce an ultrasonic knife with a total length of about 250 mm for a frequency of 24 kHz, but still with a bend (e.g. 16°) in the mid-region of the knife.

With a knife of the above design data can be achieved which are substantially equivalent to the hand-instrument described in Swedish patent application 85 05 289-2 while still obtaining the advantages of the operator's line of vision to the tip 43 not being obstructed, the knife being no heavier than, and its length not deviating significantly from the known straight knife. The operator's sensitivity to feed-back is thus retained.

The resonance rod 28 cannot be bent in the true sense since it is then no longer easy to achieve reproducible data. Instead the curved resonance rod 28 is manufactured from a substantially stressless blank of suitable metal, e.g. a duralumin alloy, which is given a curved form, with a deflection angle $\alpha$ of 16°, for instance, by means of numerically controlled turning or milling so that the resultant resonance rod is substantially free from stress and will therefore give reproducible data. The curve is preferably continuous and may extend along most of the length of the rod (not shown).

I claim:

1. An ultrasonic knife having a an operating frequency comprising:
    a horn (2) with a tip at a remote end thereof (43) to be brought into contact with tissue; and
    a transducer unit (5) coupled to an opposite end of the horn from said remote end, such that the tip (43) is imparted with a longitudinal oscillation, said transducer unit including a vibrator portion and an angled resonance rod wherein a portion of the angled resonance rod is offset at a predetermined angle from the vibrator portion, said vibrator portion and said angled resonance rod being adapted to vibrate in resonance as a unit at the operating frequency of said knife.

2. An ultrasonic knife as claimed in claim 1, wherein said the horn (2) is connected directly to the transducer unit (5).

3. An ultrasonic knife as claimed in claim 2 wherein the transducer unit (5) comprises another resonance rod and said vibrator portion is a piezoelectric unit (20 -26) clamped between said angled resonance, one of which is curved rod and said other resonance rod.

4. An ultrasonic knife as claimed in claim 3, wherein the angled resonance rod (28) is located between the piezoelectric unit (20 - 26) and the horn (2).

5. An ultrasonic knife as claimed in any of claims 1 or 2, wherein the angled resonance rod (28) is angled to give a deflection of approximately 16°.

6. An ultrasonic knife as claimed in any of claims 1 or 2, wherein the transducer unit (5) has a length of 0.5 lambda where lambda corresponds to the longitudinal vibration wavelength of the transducer unit (5).

7. An ultrasonic knife as claimed in 6, wherein the horn (2) has a length approximately 0.7 lambda.

8. An ultrasonic knife as claimed in claims 1 or 2, wherein the transducer unit (5) and horn (2) are arranged to produce a substantially pure longitudinal oscillation for the tip (43) of the horn (2).

* * * * *